United States Patent
Pillutla et al.

(10) Patent No.: US 9,884,200 B2
(45) Date of Patent: Feb. 6, 2018

(54) APPARATUS FOR COIL POSITIONING FOR TMS STUDIES

(75) Inventors: Ravi Pillutla, Audubon, PA (US);
Vincent A. Juliana, Exton, PA (US);
Mark E. Riehl, Doylestown, PA (US)

(73) Assignee: NEURONETICS, INC., Malvern, PA (US)

( * ) Notice: Subject to any disclaimer, the term of this patent is extended or adjusted under 35 U.S.C. 154(b) by 412 days.

(21) Appl. No.: 12/045,096

(22) Filed: Mar. 10, 2008

(65) Prior Publication Data
US 2009/0227830 A1 Sep. 10, 2009

(51) Int. Cl.
*A61N 2/00* (2006.01)
*A61N 2/02* (2006.01)
*A61G 15/12* (2006.01)
*A61G 15/02* (2006.01)

(52) U.S. Cl.
CPC ............ *A61N 2/02* (2013.01); *A61G 15/125* (2013.01); *A61G 15/02* (2013.01)

(58) Field of Classification Search
CPC . A61N 2/00; A61N 2/02; A61N 2/002; A61N 2/004; A61N 2/006; A61N 2/008; A61N 2/06; A61N 2/12; A61G 15/02; A61B 19/26
USPC ........................................ 600/9–15; 606/130
See application file for complete search history.

(56) References Cited

U.S. PATENT DOCUMENTS

| | | | |
|---|---|---|---|
| 3,683,923 A | 8/1972 | Anderson | |
| 4,712,558 A | 12/1987 | Kidd et al. | |
| 4,807,618 A | 2/1989 | Auchinleck et al. | |
| 4,995,395 A | 2/1991 | Ilmoniemi et al. | |
| 5,097,833 A | 3/1992 | Campos | |
| 5,116,304 A | 5/1992 | Cadwell | |
| 5,299,569 A | 4/1994 | Wernicke et al. | |

(Continued)

FOREIGN PATENT DOCUMENTS

| | | | |
|---|---|---|---|
| EP | 998958 A3 | 12/2000 | |
| EP | 1273320 A1 | 1/2003 | |

(Continued)

OTHER PUBLICATIONS

George et al. in "Daily Repetitive Transcranial Magnetic Stimulation (rTMS) Improves Mood in Depression," NeuroReport, vol. 6, No. 14, Oct. 1995, pp. 1853-1856.

(Continued)

*Primary Examiner* — Charles A Marmor, II
*Assistant Examiner* — Carrie R Dorna
(74) *Attorney, Agent, or Firm* — Condo Roccia Koptiw LLP (57) ABSTRACT

A method and device provide simple positioning of a TMS coil relative to a coordinate system of the patient's head while allowing flexible positioning of the patient's head. The system includes a mobile console on a wheeled base that integrates various subsystems and supports a mast that, in turn, supports a coil gantry that supports a TMS coil assembly. The coil gantry includes a balance arm with a counterbalance and a halo assembly that connects to the coil. The coil gantry supports the weight of the coil and allows free movement of the coil in all dimensions for easy placement on the patient's head. A head support and coil alignment aligns the patient's head and holds the head in place relative to the coil during TMS treatment.

20 Claims, 9 Drawing Sheets

(56) References Cited

U.S. PATENT DOCUMENTS

| | | | |
|---|---|---|---|
| 5,370,117 | A | 12/1994 | McLaurin, Jr. |
| 5,655,534 | A | 8/1997 | Ilmoniemi |
| 5,707,334 | A | 1/1998 | Young |
| 5,769,778 | A | 6/1998 | Abrams et al. |
| 5,813,970 | A | 9/1998 | Abrams et al. |
| 5,828,770 | A | 10/1998 | Leis et al. |
| 5,855,582 | A | 1/1999 | Gildenberg |
| 5,916,189 | A | 6/1999 | Sullenperger et al. |
| 5,923,417 | A | 7/1999 | Leis |
| 6,061,644 | A | 5/2000 | Leis |
| 6,066,084 | A | 5/2000 | Edrich et al. |
| 6,117,066 | A | 9/2000 | Abrams et al. |
| 6,148,823 | A | 11/2000 | Hastings |
| 6,169,963 | B1 | 1/2001 | Markov |
| 6,179,771 | B1 | 1/2001 | Mueller |
| 6,198,958 | B1 | 3/2001 | Ives et al. |
| 6,241,670 | B1* | 6/2001 | Nambu .................. 600/427 |
| 6,253,109 | B1 | 6/2001 | Gielen |
| 6,256,531 | B1 | 7/2001 | Ilmoniemi et al. |
| 6,266,556 | B1 | 7/2001 | Ives et al. |
| 6,288,785 | B1 | 9/2001 | Frantz et al. |
| 6,366,814 | B1 | 4/2002 | Boveja et al. |
| 6,389,318 | B1 | 5/2002 | Zarinetchi et al. |
| 6,402,678 | B1 | 6/2002 | Fischell et al. |
| 6,418,345 | B1 | 7/2002 | Tepper et al. |
| 6,463,328 | B1 | 10/2002 | John |
| 6,480,743 | B1 | 11/2002 | Kirkpatrick et al. |
| 6,484,059 | B2 | 11/2002 | Gielen |
| 6,488,617 | B1 | 12/2002 | Katz |
| 6,497,648 | B1 | 12/2002 | Rey |
| 6,503,187 | B1 | 1/2003 | Ilmoniemi et al. |
| 6,516,213 | B1 | 2/2003 | Nevo |
| 6,516,288 | B2 | 2/2003 | Bagne |
| 6,537,197 | B1 | 3/2003 | Ruohonen et al. |
| 6,551,233 | B2 | 4/2003 | Perreault et al. |
| 6,553,326 | B1 | 4/2003 | Kirsch et al. |
| 6,560,490 | B2 | 5/2003 | Grill et al. |
| 6,567,702 | B1 | 5/2003 | Nekhendzy et al. |
| 6,571,123 | B2 | 5/2003 | Ives et al. |
| 6,572,528 | B2 | 6/2003 | Rohan et al. |
| 6,625,563 | B2 | 9/2003 | Kirsch et al. |
| 6,827,681 | B2 | 12/2004 | Tanner et al. |
| 6,830,544 | B2 | 12/2004 | Tanner |
| 6,849,040 | B2 | 2/2005 | Ruohonen et al. |
| 6,926,660 | B2 | 8/2005 | Miller |
| 6,978,179 | B1 | 12/2005 | Flagg et al. |
| 7,087,008 | B2 | 8/2006 | Fox et al. |
| 7,104,947 | B2 | 9/2006 | Riehl |
| 7,120,954 | B2 | 10/2006 | Traut et al. |
| 2002/0013612 | A1 | 1/2002 | Whitehurst |
| 2002/0087201 | A1 | 7/2002 | Firlik et al. |
| 2002/0091419 | A1 | 7/2002 | Firlik et al. |
| 2002/0103515 | A1 | 8/2002 | Davey et al. |
| 2002/0123780 | A1 | 9/2002 | Grill et al. |
| 2002/0160436 | A1 | 10/2002 | Markov et al. |
| 2002/0169355 | A1 | 11/2002 | Rohan et al. |
| 2003/0004392 | A1 | 1/2003 | Tanner et al. |
| 2003/0023159 | A1 | 1/2003 | Tanner |
| 2003/0028072 | A1 | 2/2003 | Fischell et al. |
| 2003/0050527 | A1 | 3/2003 | Fox et al. |
| 2003/0065243 | A1 | 4/2003 | Tanner |
| 2003/0073899 | A1 | 4/2003 | Ruohonen et al. |
| 2003/0074032 | A1 | 4/2003 | Gliner |
| 2003/0082507 | A1 | 5/2003 | Stypulkowski |
| 2003/0088274 | A1 | 5/2003 | Gliner et al. |
| 2003/0097161 | A1 | 5/2003 | Firlik et al. |
| 2003/0125786 | A1 | 7/2003 | Gliner et al. |
| 2003/0130706 | A1 | 7/2003 | Sheffield et al. |
| 2004/0010177 | A1 | 1/2004 | Rohan et al. |
| 2004/0016057 | A1 | 1/2004 | Traut et al. |
| 2004/0019370 | A1 | 1/2004 | Gliner et al. |
| 2004/0077921 | A1 | 4/2004 | Becker et al. |
| 2004/0127942 | A1 | 7/2004 | Yomtov et al. |
| 2004/0153129 | A1 | 8/2004 | Pless et al. |
| 2005/0021104 | A1 | 1/2005 | DiLorenzo |
| 2005/0049486 | A1* | 3/2005 | Urquhart et al. .............. 600/429 |
| 2005/0124848 | A1 | 6/2005 | Holzner |
| 2005/0148808 | A1 | 7/2005 | Cameron et al. |
| 2005/0216071 | A1 | 9/2005 | Devlin et al. |
| 2005/0228209 | A1 | 10/2005 | Schneider et al. |
| 2005/0234286 | A1 | 10/2005 | Riehl et al. |
| 2005/0256539 | A1 | 11/2005 | George et al. |
| 2006/0161039 | A1* | 7/2006 | Juliana et al. .................... 600/9 |
| 2006/0287566 | A1 | 12/2006 | Zangen et al. |

FOREIGN PATENT DOCUMENTS

| | | |
|---|---|---|
| JP | 63-234962 A | 9/1988 |
| JP | 7-67972 A | 3/1995 |
| JP | 8-24298 A | 1/1996 |
| JP | 8-71168 A | 3/1996 |
| JP | 11-178809 A | 7/1999 |
| JP | 2002-538885 A | 11/2002 |
| JP | 2003-126056 A | 5/2003 |
| JP | 2003-180649 A | 7/2003 |
| JP | 2006-520671 A | 9/2006 |
| JP | 2007-508853 A | 4/2007 |
| JP | 2007-526027 A | 9/2007 |
| JP | 2008-505662 A | 2/2008 |
| JP | 2008-528108 A | 7/2008 |
| WO | WO 1999/064884 | 12/1999 |
| WO | WO 2000/54690 A1 | 9/2000 |
| WO | WO 2000/074777 A1 | 12/2000 |
| WO | WO 2001/012236 A2 | 2/2001 |
| WO | WO 2001/028622 A2 | 4/2001 |
| WO | WO 2001/97906 A2 | 12/2001 |
| WO | WO 2002/009811 A1 | 2/2002 |
| WO | WO 2002/031604 A1 | 4/2002 |
| WO | WO 2002/032504 A2 | 4/2002 |
| WO | WO 2002/072194 A2 | 9/2002 |
| WO | WO 2002/085449 A2 | 10/2002 |
| WO | WO 2002/085454 A1 | 10/2002 |
| WO | WO 2002/089902 A2 | 11/2002 |
| WO | WO 2002/094997 A2 | 11/2002 |
| WO | WO 2003/035163 A2 | 5/2003 |
| WO | WO 2003/082405 A1 | 10/2003 |
| WO | 2003/098268 A | 11/2003 |
| WO | WO 2003/090604 A2 | 11/2003 |
| WO | WO 2004/080526 A2 | 9/2004 |
| WO | WO 2004/100765 A2 | 11/2004 |
| WO | WO 2005/000401 A1 | 1/2005 |
| WO | WO 2005/065768 A1 | 7/2005 |
| WO | WO 2005/067610 A2 | 7/2005 |

OTHER PUBLICATIONS

Pascual-Leone et al. in "Rapid-Rate Transcranial Magnetic Stimulation of Left Dorsolateral Prefrontal Cortex in Drug-Resistant Depression," The Lancet, vol. 348, Jul. 27, 1996, pp. 233-237.

Wassermann, E.M., "Repetitive Transcranial Magnetic Stimulation: An Introduction and Overview", *CNS Spectrums, The International Journal of Neuropsychiatric Medicine*, Jan. 1997, 7 pages.

Hess et al., "Magnetic Stimulation of the Human Brain: Influence of Size and Shape of the Stimulating Coil", Motor Disturbances II, A Selection of Papers Delivered at the 2nd Congress of the International Medical Society of Motor Disturbances Held at, Rome, Italy, Jun. 2-4, 1988, Published in Sep. 1990, Academic Press, 3, 31-42.

Baudewig et al., "Functional MRI of Cortical Activations Induced by Transcranial Magnetic Stimulation (TMS)", Brain Imaging-Neuro Report, vol. 12, No. 16, Nov. 16, 2001, 3543-3548.

Bohning et al., "A Combined TMS/fMRI Study of Intensity-Dependant TMS over Motor Cortex", Society of Biological Psychiatry, vol. 45, No. 4, Feb. 15, 1999, 385-394.

Bohning et al., "A TMS Coil Positioning/Holding System for MR Image-Guided TMSInter leaved with fMRI", Clinical Neurophysiology, vol. 114, No. 11, Nov. 2003, 2210-2219.

Bohning et al., "BOLD-fMRI Response to Single-Pulse Transcranial Magnetic Stimulation (TMS)", Journal of Magnetic Resonance Imaging, vol. 11, No. 6, Jun. 2000, 569-574.

George et al., "A Controlled Trial of Daily Left Prefrontal Cortex TMS for Treating Depression", Society of Biological Psychiatry, vol. 48, No. 10, Nov. 15, 2000, 962-970.

(56) References Cited

OTHER PUBLICATIONS

Grafman, J., "TMS as a Primary Brain Mapping Tool", Transcranial Magnetic Stimulation in Neuropsychiatry, First Edition, American Psychiatric Press, 2000, 115-140.

Lisanby et al., "Sham TMS: Intracerebral Measurement of the Induced Electrical Field and the Induction of Motor-Evoked Potentials", Society of Biological Psychiatry, vol. 49, No. 5, Mar. 1, 2001, 460-463.

Loo et al., "Transcranial Magnetic Stimulation (TMS) in Controlled Treatment Studies: Are Some "Sham" Forms Active?", Society of Biological Psychiatry, vol. 47, No. 4, Feb. 15, 2000, 325-331.

Lorberbaum, J. P., "Safety Concerns of TMS", Transcranial Magnetic Stimulation in Neuropsychiatry, First Edition, American Psychiatric Press, 2000, 141-161.

Nahas et al., "Left Prefrontal Transcranial Magnetic Stimulation (TMS) Treatment of Depression in Bipolar Affective Disorder: A Pilot Study of Acute Safety and Efficacy", Bipolar Disorders, vol. 5, No. 1, Feb. 2003, 40-47.

Nahas et al., "Unilateral Left Prefrontal Transcranial Magnetic Stimulation (TMS) Produces Intensity-Dependent Bilateral Effects as Measured by Interleaved BOLD fMRI", Society of Biological Psychiatry, vol. 50, No. 9, Nov. 1, 2001, 712-720.

Pridmore, S., "Substitution of Rapid Transcranial Magnetic Stimulation Treatments for Electroconvulsive Therapy Treatments in a Course of Electroconvulsive Therapy", Depression and Anxiety, vol. 12, No. 3, 2000, 118-123.

Ruohonen, J., "Electroencephalography Combined with TMS", BioMag Laboratory, Helsinki University Central Hospital, Oct. 6, 1999, 22 pages.

\* cited by examiner

APPARATUS FOR COIL POSITIONING FOR TMS STUDIES

FIELD OF THE INVENTION

The present invention relates to an apparatus for precisely positioning a medical instrument with respect to a patient and, more particularly, to a positioning system for precisely and repeatably positioning a transcranial magnetic stimulation coil at the treatment position of a patient.

BACKGROUND OF THE INVENTION

Current methods of placement and positioning of coils for Transcranial Magnetic Stimulation (TMS) studies are either manual methods or approaches designed for research that require expensive and complex imaging or computational systems to determine three dimensional spatial coordinates for positioning reference. These techniques have severe clinical limitations. The manual methods do not provide a convenient means for repeated and accurate placement, while the three dimensional spatial methods based on imaging modalities are expensive, time consuming, and not conducive to clinical use. A positioning technique for clinical use is desired that provides a simple way for the operator to perform repeated and accurate coil placement for TMS studies and treatments in a time-efficient and inexpensive manner.

Manual Methods

In accordance with the conventional manual placement and position marking technique, a treatment position on the patient's head or a position used to find a treatment position, such as the patient's motor threshold position (MTP), is determined by moving the coil near a predicted area determined by patient anatomical landmarks until the desired motor response is achieved. The position is marked, for example, with an ink mark on the patient's head. In the case of using the TMS coil for treatment of depression, for example, the TMS therapy position is determined by moving the coil from the MTP along a line in the anterior direction a prescribed distance (a widely accepted distance is 5 cm). The Therapy Position (TXP) is then marked on the patient (e.g., with ink) so it can be easily found in subsequent therapy sessions.

The most common method of localization used for TMS studies is described by George et al. in "Daily Repetitive Transcranial Magnetic Stimulation (rTMS) Improves Mood in Depression," NeuroReport, Vol. 6, No. 14, October 1995, pp. 1853-1856, and by Pascual-Leone et al. in "Rapid-Rate Transcranial Magnetic Stimulation of Left Dorsolateral Prefrontal Cortex in Drug-Resistant Depression," The Lancet, Vol. 348, Jul. 27, 1996, pp. 233-237. Simply stated, in these methods the coil is first moved over the area of the left motor cortex until stimulation of the contralateral abductor pollicis brevis muscle (APB) is attained. This position is the motor threshold position (MTP) and is typically located on a line between the left auditory meatus (i.e. ear canal) and the vertex of the head, at a point about ½ to ⅔ of the distance to the vertex. In the case of excitatory stimulation of the left prefrontal cortex for the treatment of depression, for example, the TXP is located by starting at the MTP and moving 5 cm toward the midpoint between the tip of the nose and the nasion (protuberance just above the bridge of the nose). More details of techniques for determining the MTP are also described in U.S. Pat. No. 7,104,947, the contents of which are incorporated herein by reference.

The shortcomings of such manual methods are that precisely determining the line from the MTP to the TXP is difficult, marks applied to the patient that can wash off between treatment sessions are cosmetically undesirable, the coil may not be comfortably held at the TXP throughout a therapy session, and the technique is highly operator dependent and not conducive to repeatable and accurate positioning.

The problem of applying marks to the patient has been addressed in the art by applying a swim cap or similar conformal headgear to the patient and marking the headgear rather than the patient. Of course, this approach requires careful registration of the headgear during subsequent therapy sessions, which is crude, imprecise, and highly operator dependent. Moreover, such an approach still requires accurate coil placement and a mechanism for holding the coil in place.

Complex Imaging/Computational Systems

The Brainsight™ System developed by Rogue Research, Inc. of Montreal, Canada and distributed by Magstim is complex and is designed primarily for research purposes. This system uses diagnostic images from MRI or PET systems to determine the spatial relationship between internal anatomy and external landmarks and then aligns to the external landmark for therapy or other studies requiring accurate localization. While this approach is useful for research purposes, it is highly impractical and complex and is thus not usable in general clinical practice. Moreover, such techniques have generally been used to overlay coordinate systems onto images and not for identifying particular treatment positions for specific therapies.

Robotic Arms for Holding TMS Coils

U.S. Pat. Nos. 6,266,556 and 7,087,008 include descriptions of methods in which a robotic arm is operatively coupled to the TMS coil for positioning the coil with respect to the patient and holding the coil in place during TMS treatment. A similar technique using a robotic arm for coil placement is also disclosed in U.S. Pat. Nos. 6,827,681 and 6,830,544. These patents further disclose a technique for modeling the spatial structure of the patient's brain for determining the proper stimulation position using a stimulation model. While these techniques provide controlled movement and placement of the coil, they are quite expensive and do not provide for repeatable placement of the coil with respect to a particular patient's head in a clinical setting. As a result, the manual and/or complex imaging techniques described above must also be used for placement of the coil with respect to the patient.

Positioning TMS Coils Relative to Fixed Head Position

U.S. Patent Publication No. 2005/0148808 to the present assignee describes a TMS coil positioning system in which the patient's head is fixed and the TMS coil is fixed at a treatment position in the coordinate system of the patient's head. The position in the coordinate system is recorded for use in subsequent clinical sessions. In an exemplary embodiment, the positioner assembly is a mechanical system that supports the weight of the TMS coil and allows the operator to freely move the TMS coil to search for the treatment position and/or the patient's motor threshold position (MTP). Once the MTP is determined, the positioner assembly requires a single adjustment of the magnet position to locate the treatment position (TXP) where the coil is locked in place for the duration of the TMS therapy. By recording the positions of the different adjustable components in the respective coordinate directions of the coordinate system of the patient's head, exact repositioning of the TMS coil for the patient during a subsequent clinical visit is made possible without use of expensive imaging equipment.

The apparatus includes three basic components including (1) a headset assembly that accepts the patient's head and fixes its position, (2) a coil positioner assembly that accepts the headset assembly and holds the headset assembly and the patient's head at a fixed position, controls positioning of the TMS coil within a coordinate system defined about the fixed position, and holds the TMS coil in place at a treatment position during treatment, and (3) an alignment strip applied at a position in registration with an anatomical landmark of the patient including at least one registration mark for aligning the patient's head within the headset assembly. Each of these components working together permit the coil assembly to be located in coordinates with respect to the patient's head such that the treatment may be repeated during a subsequent visit by repeating the coordinates. However, such a system requires the treatment coil to be affixed to the positioning apparatus and the patient's head to remain fixed relative to the apparatus during treatment. A coil positioning system and treatment apparatus is desired that physically separates the functions of supporting the weight of the coil from the alignment function so that the coil can be easily placed or removed and so that the patient can be situated in a range of positions, thereby increasing the patient's comfort and acceptance of the TMS treatment.

Thus, the need for a simple, cost-effective and intuitive way to accurately and repeatably position the coil for TMS therapy in a clinical setting without fixing the patient in one position during treatment has not been met in the prior art. The present invention addresses this need.

SUMMARY OF THE INVENTION

The invention addresses the above-mentioned limitations in the prior art through use of a mechanical device that provides simple positioning of the TMS coil relative to the patient's head without requiring the patient to be in one particular position. In particular, the device of the invention repeatably positions a transcranial magnetic stimulation (TMS) coil with respect to a patient to receive treatment. In an exemplary embodiment, the device includes a head support that supports a patient's head, a coil alignment assembly that aligns the TMS coil with the patient's head in a fixed orientation for treatment, and a coil gantry that supports the weight of the TMS coil and is guided by the coil alignment assembly to a treatment location on the patient's head for patient treatment. The coil gantry includes a multi-axis support that allows adjustment of the pitch, roll and yaw of the TMS coil for seating of the TMS coil against the patient's head. The coil gantry may also include a mast that supports a balance arm, where the balance arm has the TMS coil on one end thereof and a counterbalance on another end thereof. In exemplary embodiments, the multi-axis support comprises a ball and socket arrangement.

The device of the invention may further be configured so that the mast is mounted on a mobile console having wheels. In an exemplary embodiment, a display is mounted on the mobile console. The display is adapted to accept inputs from a user (clinician) representing measurements of the pitch, roll and yaw of the TMS coil and position measurements of the patient's head in the coil alignment assembly. The coil gantry may also include at least one release to lock brake that, when released, prohibits movement of the TMS coil in one or more of the pitch, roll, and yaw directions, thus facilitating coil placement.

The device of the invention is configured with respect to a treatment chair adapted to accept the patient and adapted to accept the patient's head in the head support when the patient is seated in the treatment chair. Once the patient is positioned in the treatment chair, the position measurements of the patient's head are taken, and a side pad that is positioned against the patient's head opposite the TMS coil during treatment is pushed up against the patient's head. The combination of the coil and the side pad on opposite sides of the patient's head functions to keep the patient's head relatively still.

The coil alignment assembly of the invention is preferably adapted to take position measurements of the patient's head to facilitate placement of the patient's head from one treatment session to the next. For example, the coil alignment assembly may include a superior oblique angle guide including an angle indicator that indicates an angle of the superior oblique angle guide with respect to the patient's mid-sagittal plane. The coil alignment assembly may also include a pivot arm that supports an anterior/posterior guide that moves in a plane parallel to the patient's anterior/posterior axis and allows the anterior/posterior guide to rotate through a range of superior oblique angles on either side of the mid-sagittal plane of the patient's head, where the angles are measured by the angle indicator of the superior oblique angle guide. In addition, the anterior/posterior guide may support a lateral canthus guide oriented in the patient's superior/inferior direction for aligning with at least one anatomical landmark of the patient's head. The lateral canthus guide may include a scale that indicates a reference position for aligning the patient's head for repeatable positioning of the patient's head from treatment session to treatment session. The lateral canthus guide may alternatively include an alignment laser for alignment with the anatomical landmarks. A coil angle indicator also may be attached to an end of the anterior/posterior guide and include a scale for measuring the angle of the coil with respect to a center location of the anterior/posterior guide.

To facilitate alignment of the patient's head, alignment straps may also be applied at a position in registration with an anatomical landmark of the patient. The alignment straps may, for example, include a registration mark for aligning the patient's head within the coil alignment assembly. The alignment straps are typically applied to the patient's head so as to restrain the patient's head in the nodding and left/right positions. In an exemplary embodiment, the alignment straps are aligned with the patient's nose and affixed to the patient's forehead to define a mid-sagittal plane. A crown strap wraps from the back of the patient's head over a crown of the patient's head to an alignment position on a lateral strap that wraps around the respective sides of the patient's head and that is attached to the head support so as to center the patient's face in the left/right direction in the mid-sagittal plane.

BRIEF DESCRIPTION OF THE DRAWINGS

The above and other features and advantages will become apparent to those skilled in the art based on the following detailed description of the drawing figures, of which.

DETAILED DESCRIPTION OF ILLUSTRATIVE EMBODIMENTS

A detailed description of an illustrative embodiment of the present invention will now be described with reference to FIGS. 1-16. Although this description provides a detailed example of a possible implementation of the present invention, it should be noted that these details are intended to be exemplary and in no way delimit the scope of the invention.

A TMS system is a computerized electromechanical instrument that produces and delivers brief duration rapidly alternating, or pulsed, magnetic fields to induce electrical currents directed at localized regions of the cortex. The present invention is designed to position a TMS coil of the TMS system for treatment of central nervous system disease states using TMS therapies. While an exemplary embodiment of the invention is described with respect to the excitatory stimulation of the left prefrontal cortex for the treatment of depression, those skilled in the art will appreciate that the apparatus and techniques of the invention may be used to apply TMS therapies to many other central nervous system targets for the treatment of numerous other central nervous system diseases. For example, the positioning device of the invention may be used to position the TMS over the right prefrontal cortex of a patient for low frequency inhibitory stimulation in the treatment of depression. Those skilled in the art will further appreciate that the positioning device of the invention also may be used to position a TMS coil for the treatment of: epilepsy (above seizure locus), schizophrenia (at Wernicke's Area), Parkinson's Disease, Tourette's Syndrome, Amyotrophic Lateral Sclerosis (ALS), Multiple Sclerosis (MS), Alzheimer's Disease, Attention Deficit/Hyperactivity Disorder, obesity, bipolar disorder/mania, anxiety disorders (panic disorder with and without agoraphobia, social phobia a.k.a. Social Anxiety Disorder, Acute Stress Disorder, Generalized Anxiety Disorder), Post-traumatic Stress Disorder (one of the anxiety disorders in DSM), obsessive compulsive disorder (one of the anxiety disorders in DSM), pain (migraine, trigeminal neuralgia), chronic pain disorders (including neuropathic pain such as pain due to diabetic neuropathy, post-herpetic neuralgia, and idiopathic pain disorders such as fibromyalgia and regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury and regeneration/rehabilitation, head injury, sleep deprivation reversal (DARPA), primary sleep disorders (primary insomnia, primary hypersomnia, circadian rhythm sleep disorder), cognitive enhancements, dementias, premenstrual dysphoric disorder (PMS), Drug delivery systems (changing the cell membrane permeability to a drug), induction of protein synthesis (induction of transcription and translation), stuttering, aphasia, dysphagia, essential tremor, Magnetic Seizure Therapy (MST), and other central nervous system disorders that may treated by the application of a magnetic field at particular locations in the brain. Of course, in each case, the treatment positions may vary; however, in each case the positioning device of the invention is useful in finding the treatment location in a repeatable manner and holding the TMS coil in the treatment position during therapy.

System Configuration

Figure 1:
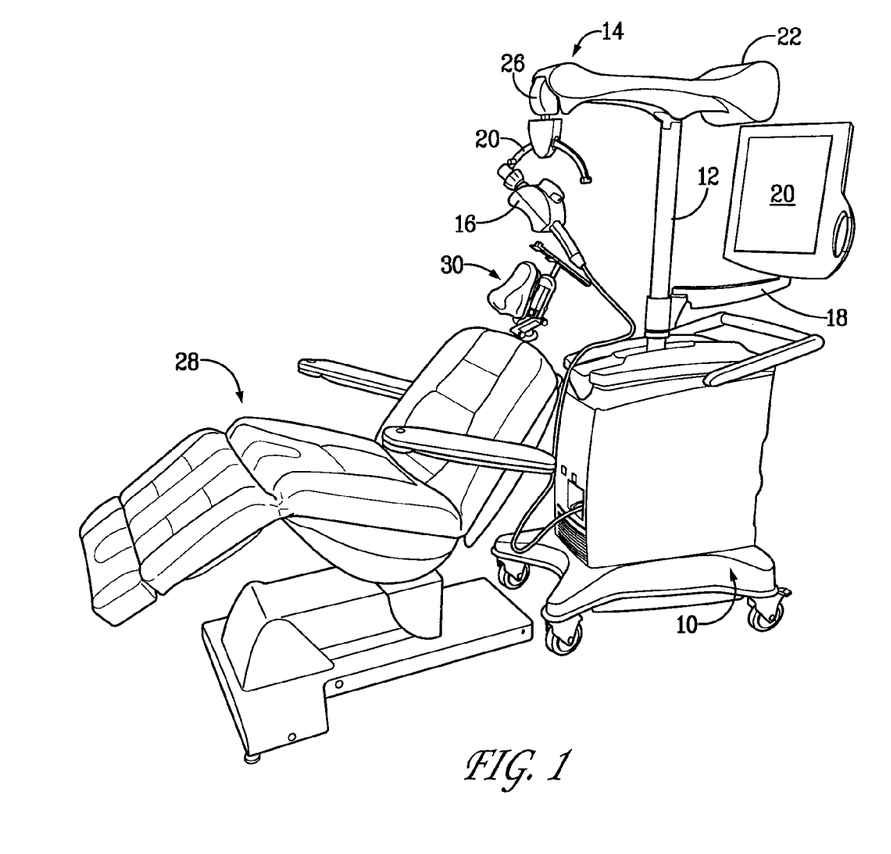
FIG. 1 illustrates the basic configuration of a TMS system incorporating the invention.

As illustrated in FIG. 1, the basic configuration of a TMS system incorporating the invention includes the following components:

Mobile Console 10 is an enclosed module that forms the TMS system's wheeled base and integrates various subsystems into a single package. It houses a processor module and a power module (not shown) and supports the mast 12 that, in turn, supports coil gantry 14 that supports coil 16 and the display arm 18 that supports the display 20. The Mobile Console 10 is the central workstation for a TMS procedure and is the main control center for all TMS system subsystems.

System Software—A computer software application running on the processor module (not shown) provides a TMS system graphical user interface on display 20 and incorporates work flow management to guide the system user (clinician) through a TMS procedure, and also supervises and controls various subsystems. The TMS System Software controls all internal system functions, monitors system status to ensure safe operation and provides the user with a graphical means to manage the course of TMS treatment. User interaction with the System Software is provided via touch screen display 20 including touch-activated images of alphanumeric keys and buttons for user interaction with the system. The display 20 provides graphic representations of system activity, messages, and alarms. Interactive buttons, fields, and images also are displayed that enable the user to direct and interact with system functions, such as entering data, starting and stopping treatment, and running diagnostics.

Coil 16 includes an enclosed electromagnet that is mounted to the coil gantry 14 which supports its weight as it is placed against the patient's head. The coil 16 generates and applies a pulsed magnetic field to tissue immediately beneath the coil 16 in response to commands from the processor and power modules. The magnetic field penetrates the skull and reaches the patient's cortex when the coil is placed against the patient's head. This pulsed field is controlled by the TMS system power module and system software in response to user settings. The coil gantry 14 includes a lateral translation table within the Mobile Console 10, a vertical mast 12, a balance arm with counterbalance 22, and a halo assembly 24 that connects to the coil 16 as shown in FIG. 1. The coil gantry 14 supports the weight of the coil 16 and allows free movement of the coil 16 in all dimensions for easy placement on the patient's head. Coil gantry 14 also incorporates electro-mechanical brakes of the "release to lock" type that automatically lock four degrees of motion to hold the coil 16 in place when a push-button switch on the coil 16 is released, or when commanded under software control. There are three degrees of freedom in the mechanism 26 that immediately connects to the coil 16 (the "wrist") of the balance arm 22. There is a manual brake to stop motion of the halo ring 24 and a manual brake to adjust coil axial rotation resistance. The display arm 18 moves separately from the coil gantry 14 along a horizontal plane, enabling the user to adjust the position of the display 20.

Treatment Chair 28 is an operator controlled, adjustable chair that positions the patient comfortably at a desirable height and angle for TMS treatment and provides lumbar support. The treatment chair 28 is adjustable to accommodate the patient in a comfortable reclining position such that the patient's coronal plane is approximately 30°-75° from horizontal during treatment and includes a separate attachment for the chair that provides adjustable head support and includes a guidance apparatus in accordance with the present invention to aid in positioning the coil 16 against the patient's head. The treatment chair 28 is an electromechanical device on which the patient is seated during treatment with the TMS system and resembles the type of chair used in dental treatment environments. The treatment chair 28 may include a pushbutton control unit (wired or wireless) that adjusts the chair height, the patient's reclining position, and the patient's leg support. The treatment chair 28 also may include a substantial base for overall stability and a built-in adjustable lumbar support cushion for patient comfort. The seat tilt feature helps lift the patient's seat to avoid patient slouching.

Head Support and Coil Alignment Unit 30 is an electromechanical device in accordance with the present invention that comprises several parts that are designed to provide maximum patient comfort and reliable coil position measurement of the patient's motor threshold (MT) location and/or TMS treatment location. The Head Support and Coil Alignment Unit 30 aligns the patient's head and holds the head in place relative to the coil during TMS treatment. The individual parts of the Head Support and Coil Alignment Unit 30 are identified in FIG. 3.

Figure 2:
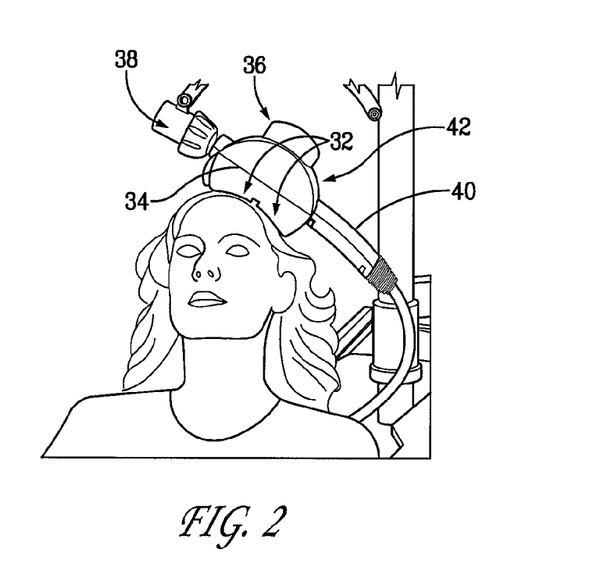
FIG. 2 illustrates the coil assembly of the TMS system of FIG. 1.

As shown in FIG. 2, the coil 16 generally includes a treatment surface 32, a front side 34, a top side 36, an axle 38 about which the coil 16 may rotate, a handle 40 for easy maneuvering of the coil 16, and coil control buttons 42 that may apply a coil brake (not shown) or the like. The coil 16 is positioned against the patient's head during TMS treatment using techniques to be explained in more detail below.

Figure 3:
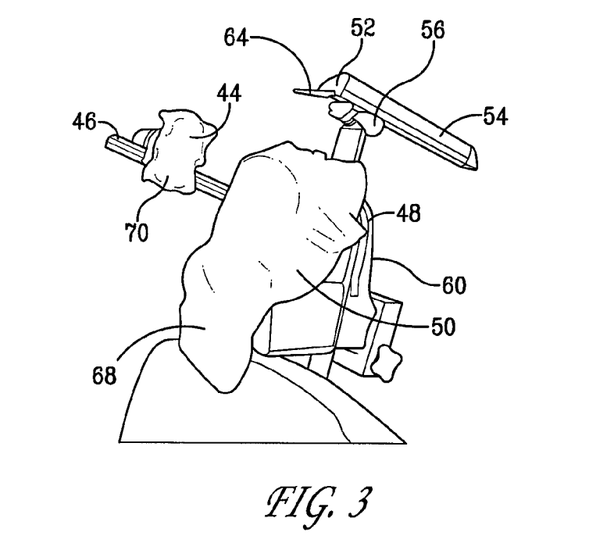
FIG. 3 illustrates the head support and coil alignment assembly of the TMS system of FIG. 1.
Figure 4:
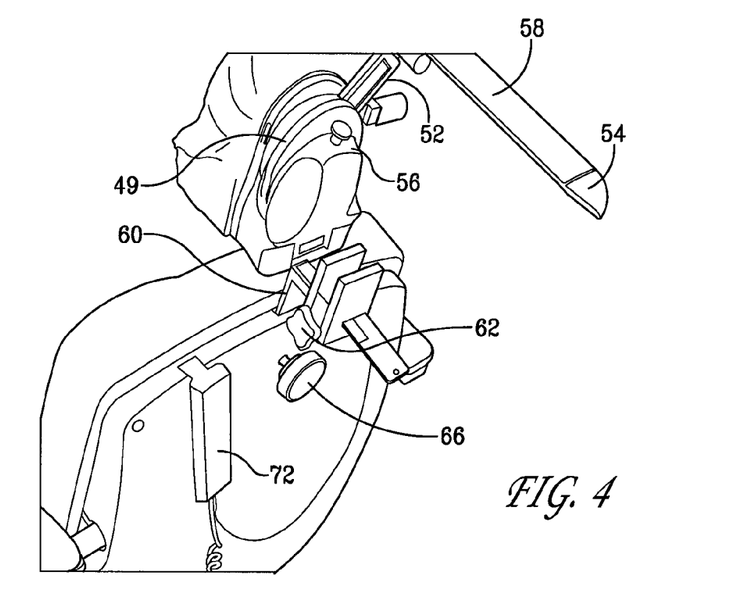
FIG. 4 illustrates the alignment knobs on the back of the head support and coil alignment assembly of FIG. 3.

As shown in FIGS. 3 and 4, the Head Support and Coil Alignment Unit 30 is mounted on the Treatment Chair 28 so as to provide a comfortable support for the patient's head during treatment sessions. The Head Support and Coil Alignment Unit 30 may be set at different heights, angles, and distances to accommodate a range of patient positions in response to patient physical characteristics. Specifically, the Head Support and Coil Alignment Unit 30 has degrees of freedom that enable the user (clinician) to adjust the head support in the anterior-posterior as well as the inferior-superior directions for patient comfort. The Head Support and Coil Alignment Unit 30 includes a side pad 44 mounted on a bracket assembly 46 that allows the side pad 44 to be moved for set up on either the left or right side of the patient's head. The user can move the side pad 44 toward or away from the side of the patient's head along the bracket assembly 46 until a comfortable position has been established.

The Head Support and Coil Alignment Unit 30 also includes a superior oblique angle (SOA) guide 48 including an angle indicator 49 (FIG. 4) located behind the head support cushion 50 associated with a pivot arm 52 that supports the anterior/posterior (AP) guide 54. The pivot arm 52 allows the AP guide 54 to be rotated through a range of superior oblique angles +/−45° from the mid-sagittal position by pressing knob 56 (FIG. 4) to disengage the AP guide 54. The AP guide 54 includes a straight flat scale 58 that aids the clinician in accurately positioning the coil. The AP guide 54 moves parallel to the patient's AP axis and provides a calibrated index of its position using the flat scale 58. The lateral canthus (LC) guide 60 (FIG. 4), on the other hand, is a flat scale oriented in the patient's superior/inferior direction and located behind the head support cushion 50. The scale on the LC guide 60 is used to indicate a reference position for aligning the patient's head to the Head Support and Coil Alignment Unit 30 via adjustment knob 62 (FIG. 4) for repeatable positioning from session to session.

A coil angle indicator 64 includes a flat curved scale that is attached to the end of the AP guide 54. Coil angle indicator 64 enables the user to record the position of the coil 16 up to 20° to the left or right of the center location. A vertical alignment knob 66 (FIG. 4) also permits the entire Head Support and Coil Alignment Unit 30 to be moved vertically with respect to the Treatment Chair 28 to better accommodate the patient.

The Head Support and Coil Alignment Unit 30 also may include a head cushion liner 68 that includes a thin, tissue-like disposable cover that is placed on the head cushion 50 as a hygienic barrier for each patient session. The Head Support and Coil Alignment Unit 30 also offers the patient further comfort through the use of the side pad 44 that may be set up both on the left or the right side of the patient's head. The side pad 44 is a replaceable foam pad that is mounted on the side pad bracket 46. During treatment, the side pad 44 is covered by a disposable side pad liner 70 that is a thin, tissue-like disposable cover that is placed on the side pad 44 as a hygiene barrier for each patient session.

Patient Positioning Procedure

For effective treatment, the patient is seated comfortably so as to be properly aligned with the TMS system. The patient is positioned at a height that provides the operator with comfortable access for positioning the TMS coil 16. The steps for finding the correct patient position using the components illustrated in FIG. 1 will now be described.

Prior to treatment, the patient must remove certain objects before activating the TMS system, including hearing aids, eyeglasses, or metal hairclips. Loose metallic objects are especially prohibited near the coil 16. Prior to seating the patient, a fresh head cushion liner 68 is placed over the head support 50 and a fresh side pad liner 70 is placed over the side pad cushion 44. The side pad positioning arm 46 is unlocked by pushing or pulling the metal locking bar to bring it to an equal distance on both sides from the Head Support and Coil Alignment Unit 30. The side pad positioning arm 46 is positioned to a vertical position and the AP arm 52 is positioned to "0" and at the "0" position on the left superior oblique angle guide 48. The LC dial is set to "0" using LC knob 56.

Once the patient is ready, the patient is correctly positioned to sit in the Treatment Chair 28. Using a chair controller 72 (FIG. 4), the Treatment Chair 28 is placed in the treatment position. The feet setting may be adjusted to patient comfort and the chair height to the user's comfort. No other adjustments should be made to the chair settings as this will hinder reproducibility of the treatment setting from session to session. The patient's head and body are centered in the chair by standing in front of the chair and directing the patient as needed to a centered position. The user then holds the head cushion 50 with one hand and uses the other hand to loosen the vertical alignment knob 66 on the back of the chair, as illustrated in FIG. 4, by turning it counterclockwise. The Head Support and Coil Alignment Unit 30 is then adjusted until the patient is comfortable. The Head Support and Coil Alignment Unit 30 is locked in place by turning the vertical alignment knob 66 clockwise until it is tight enough to hold the Head Support and Coil Alignment Unit 30 in place. Similarly, the user holds the head cushion 50 with one hand and uses the other hand to loosen the articulation adjustment knob 62 on the back of the chair. The Head Support and Coil Alignment Unit 30 is moved forward or backward until the patient is comfortable. The Head Support and Coil Alignment Unit 30 is locked in place by turning the articulation adjustment knob 62 clockwise until it is tight enough to hold the Head Support and Coil Alignment Unit 30 in place. The cushion 50 also may be used to assist in patient comfort. Once seated, the patient is instructed to get into a comfortable position that can be maintained until the end of the treatment session. The patient may also be instructed to insert ear plugs prior to treatment.

Figure 5:
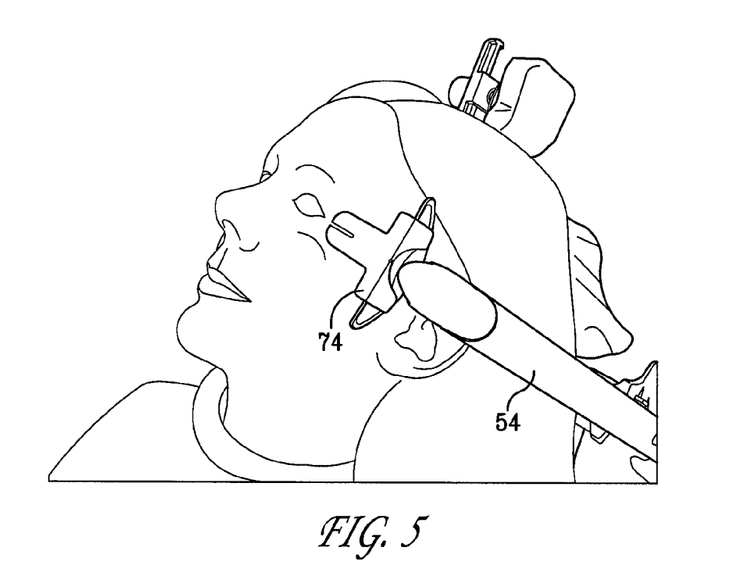
FIG. 5 illustrates how the Anterior/Posterior (AP) arm is aligned to the point of the lateral canthus of the patient.
Figure 6:
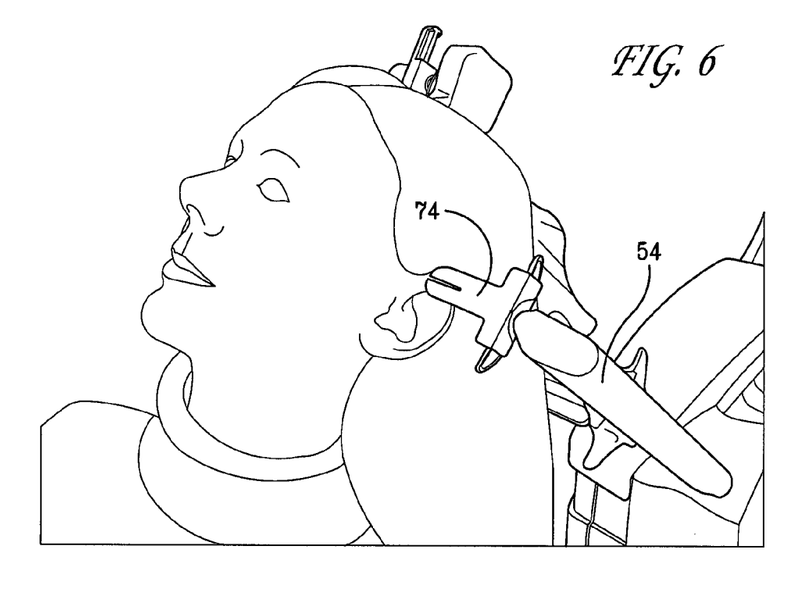
FIG. 6 illustrates how the AP arm is aligned to the patient's ear attachment to the skull.

The patient is then placed in position for a determination of the motor threshold (MT) position. First, the AP guide 54 is rotated to the patient's left side until it reaches a mechanical stop. The LC pointer 74 is attached to the AP guide 54 and the user ensures that the LC pointer 74 is close to, but not touching, the patient's head as shown in FIG. 5. Alternatively, an alignment laser may be incorporated into the AP Guide in place of the mechanical LC pointer 74 to aid in the following steps. The AP guide 54 is unlocked and slid forward to the point of the lateral canthus. The AP guide 54 is then relocked. The LC pointer 74 (or alignment laser) is adjusted until it is lined up with the lateral canthus by dialing the LC knob 56 (FIG. 4). If the lateral canthus cannot be achieved within the set range, the patient is repositioned. The AP guide 54 is then unlocked and the LC pointer 74 (or alignment laser) is used to align the LC pointer 74 to the point of the ear attachment to the skull to create a horizontal line back to the lateral canthus to the extent possible without sacrificing patient comfort (FIG. 6). The LC pointer 74 (or alignment laser) is then removed (or turned off) and the AP guide 54 is returned to the 0 position. Of course, when the alignment laser is used in place of the LC pointer 74, the beam of light from the alignment laser is used to cast a line between the corner of the patient's eye (i.e. lateral canthus) and the point of ear attachment to the skull as illustrated in FIGS. 5 and 6. Other techniques may also be used for finding the treatment position with or without finding the motor threshold position.

Figure 7:
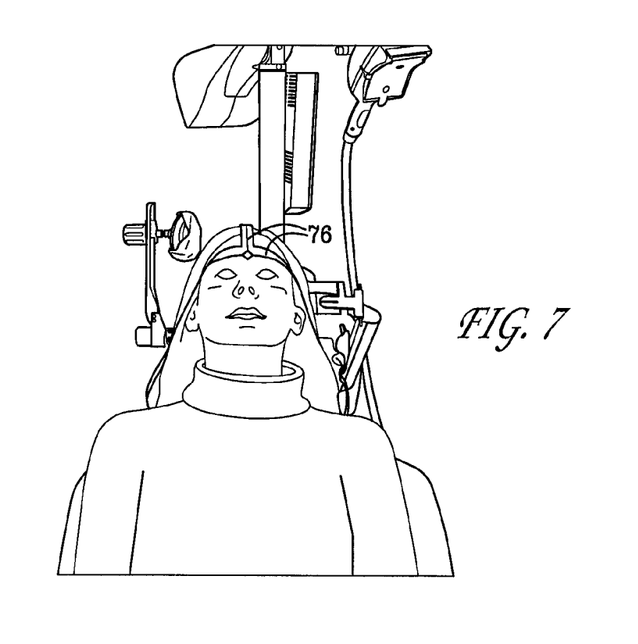
FIG. 7 illustrates how alignment straps are placed on the patient's forehead just above the eyebrow line and the pointer on the strap is placed to the center of the patient's nose.
Figure 8:
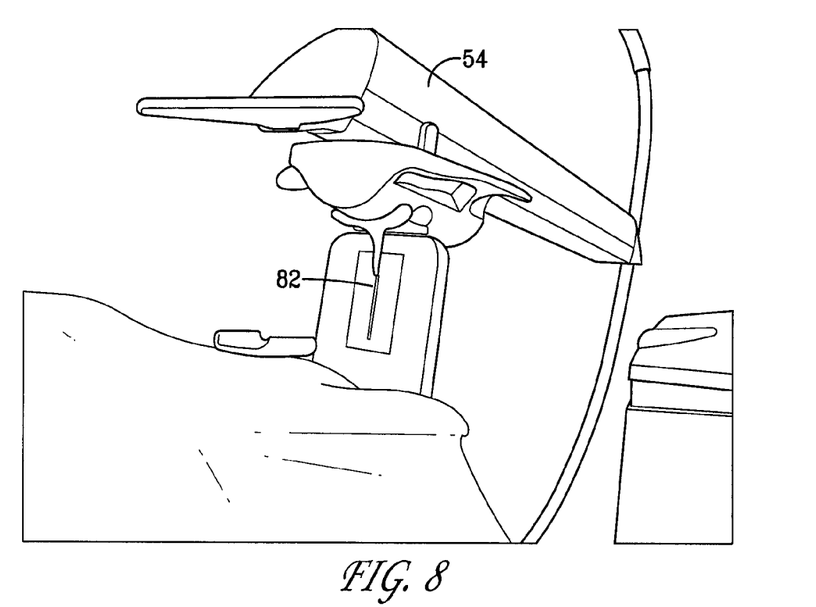
FIG. 8 illustrates alignment of the butterfly on the centering mark.
Figure 9:
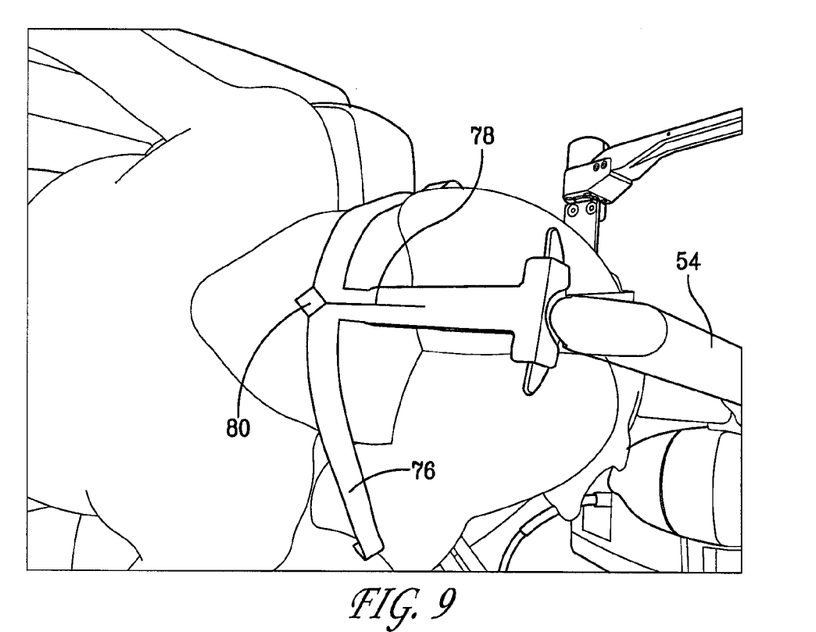
FIG. 9 illustrates adjustment of the patient's head to center position by aligning the centering pointer to the top alignment strap centering line.
Figure 10:
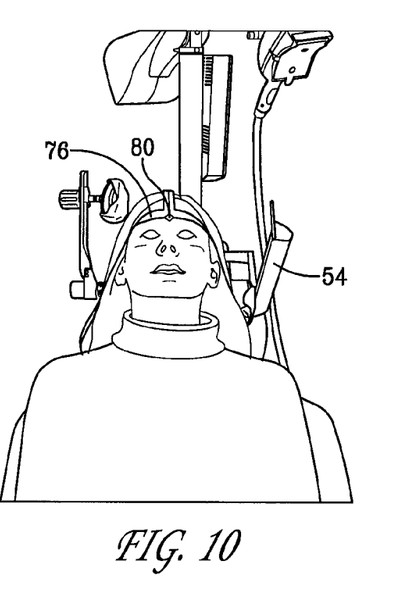
FIG. 10 illustrates the top strap attached to the top of the head support unit and the side straps attached to the side supports to ensure a centered position (centering pointer and centering strap aligned).

Next, alignment straps 76 are placed on the patient's forehead just above the eyebrow line and the pointer 78 (FIG. 9) on the strap 76 is placed to the center of the patient's nose as shown in FIGS. 7 and 9. The mid-sagittal plane is established by moving the AP guide 54 to the "0" position on the LSOA guide 48. The AP guide 54 is slid forward and the AP guide 54 is locked. The centering pointer 78 is attached to the AP guide 54, and the operator ensures that the butterfly 80 is on the centering mark 82 (FIGS. 8 and 9). The patient's head is adjusted to center position as needed by aligning the centering pointer 78 to the top alignment strap centering line of the straps 76 as shown in FIG. 9. The top strap 76 is attached to the top of the Head Support and Coil Alignment Unit 30 and the side straps 76 are attached to the side supports to ensure a centered position (centering pointer and centering strap aligned) as shown in FIG. 10. The centering pointer 78 is removed and the patient alignment is rechecked by moving the AP guide 54 back to the left LC position. The LC pointer 74 is re-attached to check that the LC position has been maintained as described above. The straps 76 are adjusted if needed to re-establish LC position and the LC pointer 74 is removed.

The patient's measurements for the LC and head support positions (vertical alignment, articulation setting) and top strap position setting are recorded at the appropriate times using the touch display 20 (FIG. 1) to enter the settings into the application program for storage.

Figure 11:
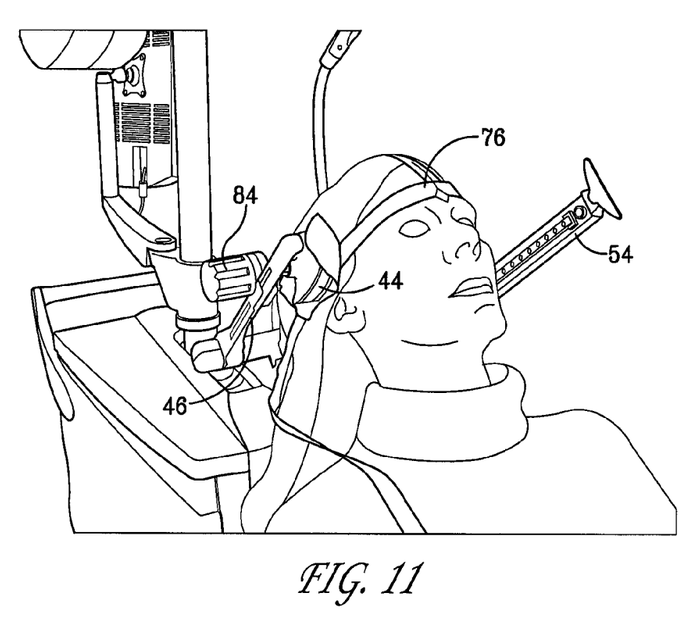
FIG. 11 illustrates the side head pad support as placed to the top and slight rear of the right ear.
Figure 12:
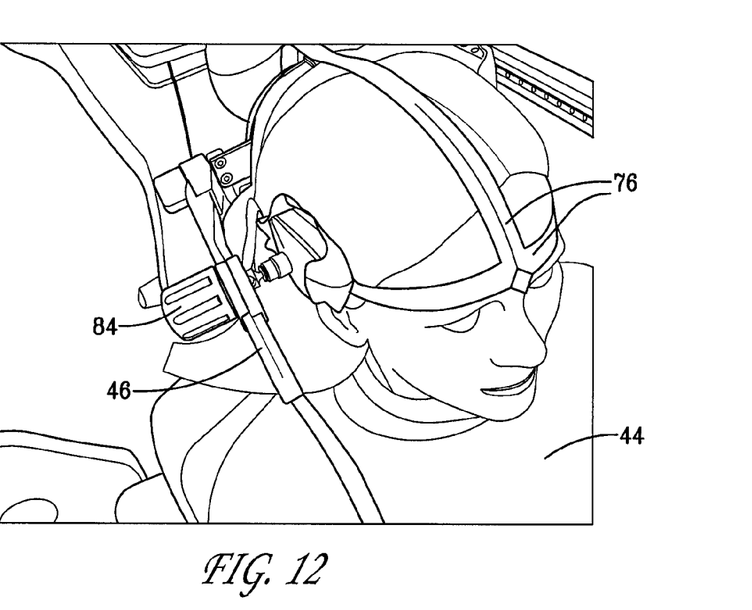
FIG. 12 illustrates the side pad mechanism slid in towards the center of the chair to apply enough support to spring the support spring approximately half way.
Figure 13:
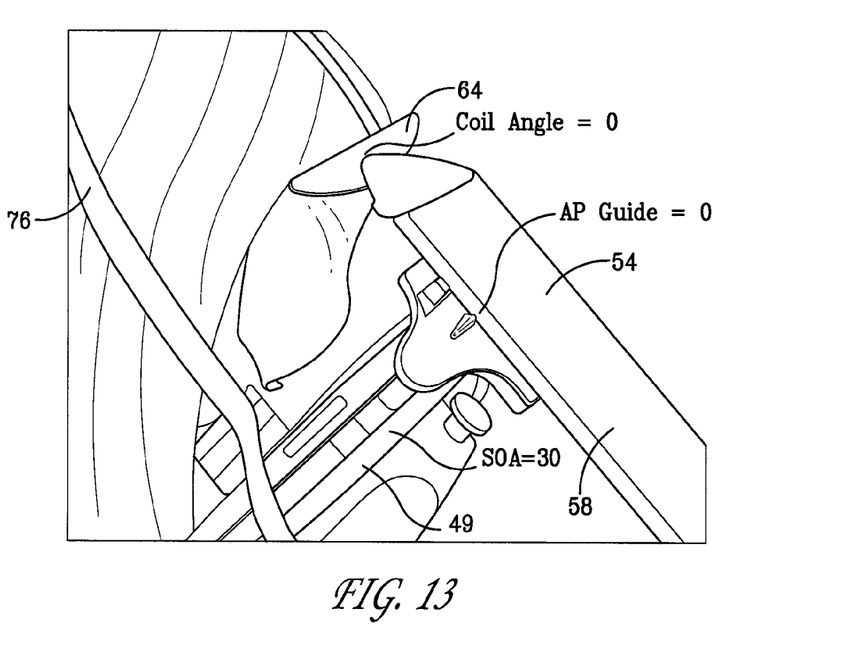
FIG. 13 illustrates the alignment features on the back of the patient's head when the patient is positioned and ready for MT location.

Once the patient is positioned and the straps are placed on the patient's head as illustrated in FIG. 10, the side pad positioning arm 46 is then brought down to a horizontal position and the side pad position is unlocked by turning the knob 84 (FIG. 11) towards the back of the Treatment Chair 28 and placing the side head pad support 44 to the top and slight rear of the right ear as shown in FIG. 11. The pad position is relocked by turning the knob 84 towards the front of the Treatment Chair 28. The side pad mechanism 46 is slid in towards the center of the Treatment Chair 28 to apply enough support to bring the support spring (not shown) approximately half way, engaged to patient comfort (head alignment may be temporarily shifted until the coil 16 is placed) as shown in FIG. 12. The side pad support mechanism 46 is locked by a ratcheting mechanism (not shown) in the pad positioning arm 46 until the pad support 44 remains in place. The user then unlocks and slides the AP guide 54 back to 0 and relocks the AP guide 54. As illustrated in FIG. 13, the SOA guide 48 is moved to the 30° mark on the left SOA scale 49 and it is ensured that the butterfly 80 is on centering line (i.e., on the patient's left side). The coil angle indicator 64 is adjusted to 0°. The patient is now ready for MT location.

Figure 14:
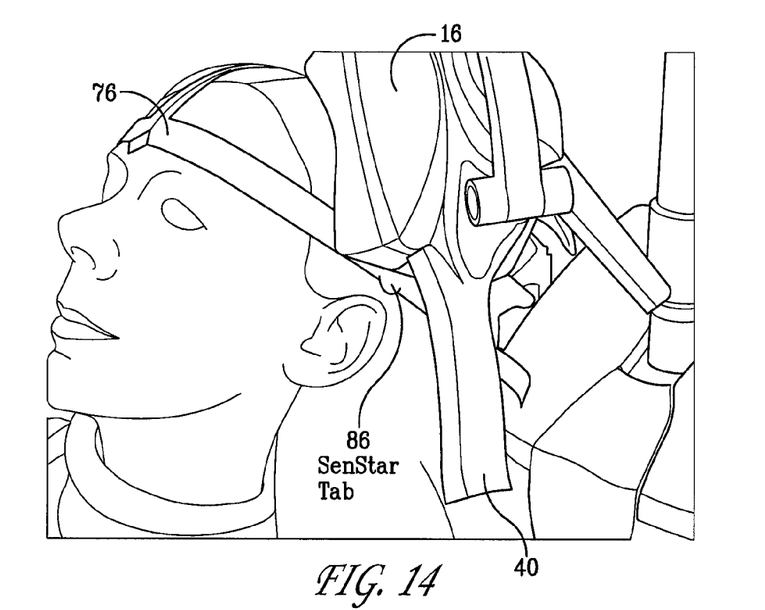
FIG. 14 illustrates the initial position of the coil for MT location where the tab is just above the patient's ear.
Figure 15:
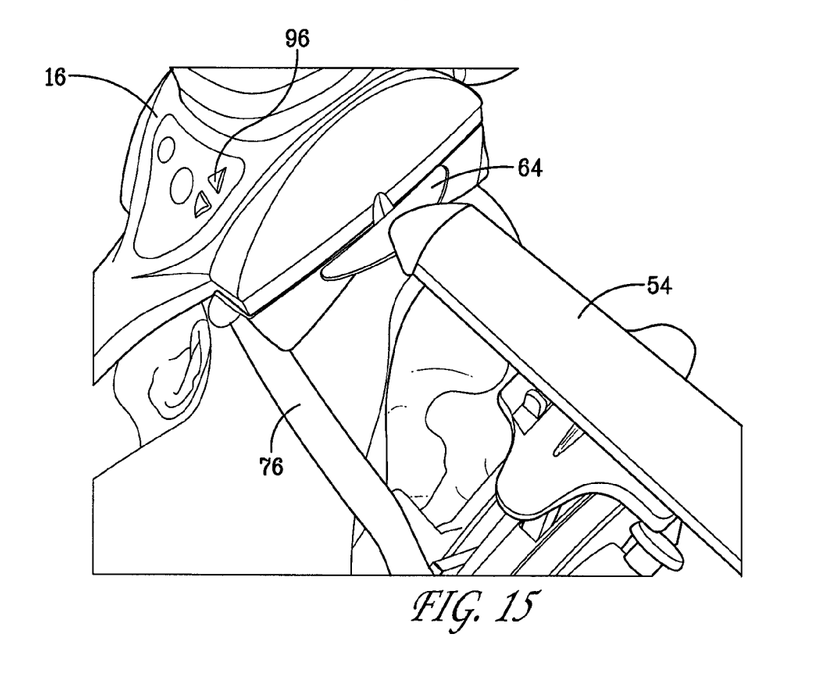
FIG. 15 illustrates the coil as placed against the left side of the patient's head ready for MT location.
Figure 16:
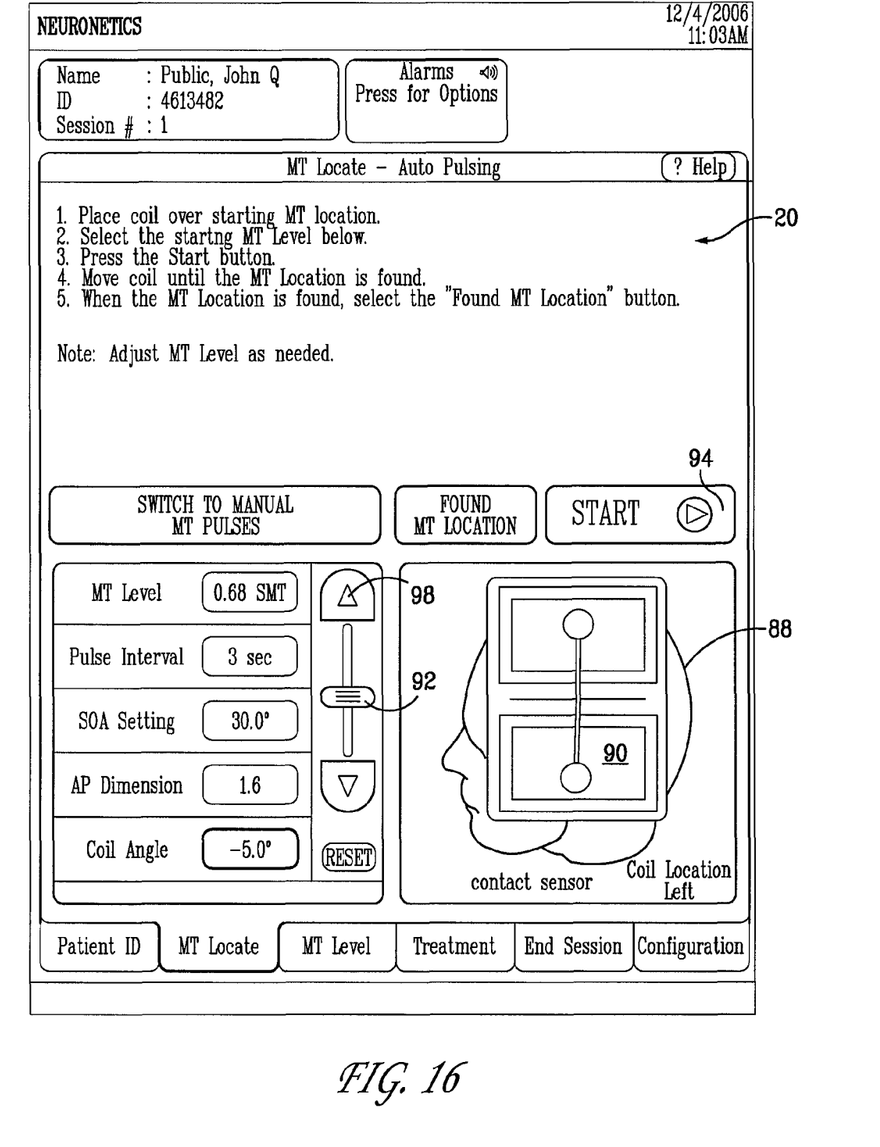
FIG. 16 illustrates the contact sensor portion of the touch screen displaying a mark indicating that the coil is making contact with the patient's head when the patient is positioned to begin MT location search.

The motor threshold (MT) location of the patient for treatment or as part of the screening process is located for each new patient by grasping the coil handle 40 and pressing and holding the brake release button 42. The user starts searching on a mid-coronal plane, which falls at the level from the top of the subject's left ear to the vertex (top) of the head. To start, the user positions the coil 16 so that the tab 86 is just above the patient's ear (FIG. 14). The user then releases the coil brake button 42. The coil 16 should now be against the left side of the patient's head, as illustrated in FIG. 15. The user views the touch screen 20 while pressing down on the coil 16 until the coil makes contact with the patient's head. As illustrated in FIG. 16, the contact sensor portion 88 of the touch screen 20 displays a mark 90 indicating that the coil 16 is making contact with the patient's head. The patient is now positioned to begin MT location search.

For automatic MT location, the patient is instructed to hold his or her right hand in a position that enables the user to observe a twitch in the right thumb (abductor pollicis brevis muscle). The coil assembly 16 is moved to search for the optimal site of the right motor cortex region of the brain. This will cause movement of the right APB muscle, which will produce a visible twitch of the patient's right thumb. The search starts on a mid-coronal plane, which falls at the level from the top of the subject's left ear to the vertex of the head. To start, the coil 16 is positioned so that the edge of the coil 16 above the handle 40 is just above the patient's ear. The brake release button 42 on the coil handle 40 is pressed and the coil 16 is moved to a possible MT location. The brake release button 42 is pressed to set the brake. To begin locating the optimal stimulation site, a slider 92 in the lower left-hand side of the touch screen display 20 is used to gradually increase the machine power output at a suprathreshold range, which is generally between 1.00 and 1.10 Standard Motor Threshold (SMT) units. The default starting power is, for example, 0.68 SMT units. The power output is increased or decreased as necessary to achieve a reliable observed thumb and forefinger twitch when the coil 16 is positioned over the optimal location.

Once the coil 16 is placed, the START button 94 on the touch-screen 20 is pressed to cause the system to automatically generate a pulse every 3-10 seconds. If the patient's thumb twitch is not observed, the coil 16 is moved to a different location on the patient's head or the MT level is increased in one of three ways:

Press the increase button 96 (FIG. 15) on the back of the coil 16.

Touch the increase arrow 98 in the MT Level section of the MT Locate display.

Touch and move the slider 92 up in the MT Level section of the MT Locate display.

The user continues the search for the patient's MT location using these steps until the optimal location is determined to isolate the (APB) thumb muscle. Once the MT location has been identified, the AP guide 54 is moved up to the coil 16 aligning the coil angle guide 64 to the center line on the side of the coil (FIG. 15). The following are the MT location coordinates and are recorded in the MT Locate screen (FIG. 16) of the application software:

Superior Oblique Angle (SOA)
Anterior/Posterior (AP)
Coil Rotation Angle.

The patient's MT level is also recorded.

Those skilled in the art will appreciate that once the patient's head is aligned in the Head Support and Coil Alignment Unit 30 that the side pad mechanism 46 pushed up against the side of the patient's head opposite the TMS coil assembly 16 prevents side-to-side movement of the patient's head when a small force is applied to the other side of the patient's head during the seating of the TMS coil assembly 16 on the patient's head. As illustrated in FIG. 1, the coil assembly 16 with its connector is mounted in a multi-axis support gantry with multiple degrees of freedom to position the TMS coil assembly 16 that together with the mast 12 fully supports the weight of the TMS coil assembly 16 and allows free motion in all axes. In particular, the multi-axis support gantry (FIG. 1) allows for adjustment of the pitch, roll and yaw of the TMS coil assembly 16 for seating of the TMS coil assembly 16 against the patient's head. In an exemplary embodiment, a counterbalance 22 helps to counteract the weight of the coil assembly against the patient's head, further increasing the patient's comfort during a therapy session.

Since the procedure is highly repeatable, the recorded positions (lateral canthus position, left superior oblique angle, anterior/posterior position, and coil rotation position) in the patient's coordinates may be used to allow a patient to be treated easily on other systems that employ the same positioning and/or coordinate systems.

Those skilled in the art also will readily appreciate that many additional modifications are possible in the exemplary embodiment without materially departing from the novel teachings and advantages of the invention. For example, the Head Support and Coil Alignment Unit 30 of the invention could be modified to target any other anatomical landmark of the patient that also produces a repeatable position relative to internal anatomy. Also, rather than searching for the MT position for use in finding a treatment position for treating depression, the system of the invention may be used to find the Wernicke's Area for treating schizophrenia or finding other treatment positions for other central nervous system disorders responsive to TMS treatments.

Also, those skilled in the art will appreciate that the multi-axis support gantry of the invention may be replaced by a suitable ball and socket arrangement that allows precise control of three-dimensional movements of the coil assembly.

Accordingly, any such modifications are intended to be included within the scope of this invention as defined by the following exemplary claims.

What is claimed:

1. A device for repeatably and non-invasively positioning a transcranial magnetic stimulation (TMS) coil with respect to a patient to receive treatment, the device comprising:
   a head support that supports a patient's head; and
   a coil alignment assembly for aligning the TMS coil with the patient's head in a fixed orientation with respect to the head support for treatment, the coil alignment assembly comprising a pivot element and a non-invasive anterior/posterior guide for guiding the alignment of the TMS coil along an anterior/posterior axis of the patient and a coil angle indicator for measuring an angle of the TMS coil with respect to a central axis of the anterior/posterior guide parallel to the patient's anterior/posterior axis, wherein the anterior/posterior guide is supported by the pivot element and is configured to extend in the anterior/posterior direction relative to pivot element, move separately from the TMS coil when non-invasively aligning the TMS coil with the patient's head and rotate through a range of superior oblique angles on either side of the mid-sagittal plane of the patient's head; and
   a coil gantry that supports the weight of the TMS coil when the TMS coil is guided by the coil alignment assembly to a treatment location on the patient's head and during patient treatment, wherein the coil alignment assembly and the coil gantry are configured separately in the device.

2. A device as in claim 1, wherein the coil gantry comprises a mast that supports a balance arm, said balance arm having said TMS coil on one end thereof and a counterbalance on another end thereof.

3. A device as in claim 2, wherein said coil gantry comprises a multi-axis support that allows adjustment of the pitch, roll and yaw of the TMS coil for seating of the TMS coil against the patient's head.

4. A device as in claim 3, wherein said multi-axis support comprises a ball and socket arrangement.

5. A device as in claim 3, wherein the coil gantry includes at least one release to lock brake that, when released, prohibits movement of the TMS coil in one or more of the pitch, roll, and yaw directions.

6. A device as in claim 2, wherein the mast is mounted on a mobile console having wheels.

7. A device as in claim 6, further comprising a display mounted on said mobile console, said display adapted to accept inputs representing measurements of the pitch, roll and yaw of the TMS coil and position measurements of the patient's head in the coil alignment assembly.

8. A device as in claim 1, further comprising a treatment chair adapted to accept the patient and adapted to accept the patient's head in the head support when the patient is seated in the treatment chair.

9. A device as in claim 1, wherein the head support includes a side pad that is positioned against the patient's head opposite the TMS coil during treatment.

10. A device as in claim 1, wherein the coil alignment assembly includes a superior oblique angle guide including an angle indicator that indicates an angle of the superior oblique angle guide with respect to the patient's mid-sagittal plane.

11. A device as in claim 1, wherein the pivot element comprises a pivot arm that supports the anterior/posterior guide that moves in a plane parallel to the patient's anterior/posterior axis and allows the anterior/posterior guide to rotate through the range of superior oblique angles on either side of the mid-sagittal plane of the patient's head.

12. A device as in claim 1, wherein the coil alignment assembly further comprises a lateral canthus guide oriented in the patient's superior/inferior direction for aligning with at least one anatomical landmark of the patient's head.

13. A device as in claim 12, wherein the lateral canthus guide comprises an alignment laser.

14. A device as in claim 1, wherein the coil angle indicator is attached to an end of the anterior/posterior guide and comprises a scale for measuring the angle of the coil with respect to a center location of the anterior/posterior guide.

15. A device as in claim 1, further comprising at least one alignment strap applied at a position in registration with an anatomical landmark of the patient, said alignment strap including at least one registration mark for aligning the patient's head within said coil alignment assembly.

16. A device as in claim 15, wherein said head support comprises a cushion for accepting a back of the patient's head and said alignment strap restrains the patient's head in the nodding and left/right positions.

17. A device as in claim 16, wherein said alignment strap is aligned with the patient's nose and affixed to the patient's forehead to define a mid-sagittal plane, and wherein said alignment strap comprises a crown strap that wraps from a back of the patient's head over a crown of the patient's head to an alignment position on the alignment strap and a lateral strap that wraps around the respective sides of the patient's head and is attached to the head support so as to center the patient's face in the left/right direction in the mid-sagittal plane.

18. The device of claim 1, wherein positional adjustment to the anterior/posterior guide is configured separately from a component of the device that controls TMS coil movement.

19. The device of claim 1, wherein the anterior/posterior guide is supported by the head support.

20. The device of claim 1, wherein the anterior/posterior guide is configured to rotate through a range of superior oblique angles from a mid-sagittal position.

* * * * *